United States Patent [19]

Chu

[11] 4,289,747

[45] Sep. 15, 1981

[54] IMMUNOLOGICAL DETERMINATION USING LECTIN

[75] Inventor: Albert E. Chu, San Mateo, Calif.

[73] Assignee: E-Y Laboratories, Inc., San Mateo, Calif.

[21] Appl. No.: 972,696

[22] Filed: Dec. 26, 1978

[51] Int. Cl.³ .................... G01N 33/48; G01T 1/00; A61K 43/00

[52] U.S. Cl. .................... 424/1; 23/230 B; 424/12; 435/7

[58] Field of Search .................... 424/1, 12; 23/230 B; 435/7

[56] References Cited

U.S. PATENT DOCUMENTS

| | | | |
|---|---|---|---|
| 3,555,143 | 1/1971 | Axen et al. | 424/1 |
| 4,053,284 | 10/1977 | Posch | 23/230 B |
| 4,098,876 | 7/1978 | Piasio et al. | 424/1 |

Primary Examiner—Benjamin R. Padgett
Assistant Examiner—Christine M. Nucker
Attorney, Agent, or Firm—Flehr, Hohbach, Test, Albritton & Herbert

[57] ABSTRACT

A method for the determination of one or more components of an immunological conjugate, e.g., antigens, of a fluid sample in a competitive or sandwich technique in which the conjugate is labelled and separated from its reactive mixture by reversible attachment to a solid surface. In a preferred embodiment, the solid surface comprises insolubilized sugar which reversibly bonds to a lectin covalently bonded to one member of the conjugate. After separation of such solid surface from the remainder of the reaction mixture, the insolubilized sugar-lectin bond is broken by contact with a sugar solution which displaces the labelled lectin compound. The immunological components including label and lectin may be preincubated in a homogeneous solution prior to reversible attachment to the sugar solid surface. For a competitive system, a sample containing antigen is incubated with a known quantity of labelled antigen and lectin-bound antibody. In the sandwich technique, the sample antigen is incubated with lectin-bound antibody and further with labelled antibody and this reaction mixture is contacted with insolubilized sugar. Either the competitive or sandwich technique are adaptable to a sequential flowthrough system with sufficient residence time to eliminate the preliminary incubation steps.

48 Claims, No Drawings

IMMUNOLOGICAL DETERMINATION USING LECTIN

Reference is made to my patent application entitled "Method for Forming an Isolated Lectin-Immunological Conjugate and Product", filed simultaneously herewith.

The invention relates to an immunochemical technique for the label analysis of one component of an immunological conjugate, e.g., antigen or antibody, in which the labelled conjugate is separated from the remainder of the reaction mixture by reversible attachment to a solid surface and thereafter is removed from the solid surface for analysis.

The common immunological assay techniques are the so-called sandwich or competitive binding technique. In the sandwich technique, sample such as serum containing an unknown concentration of antigen is immunologically reacted with antibody which is separated from the remainder of the reaction mixture. Then, the bound antigen is incubated with labelled antibody and the amount of immunologically-bound, labelled antibody is measured. In a competitive binding technique, the concentration of antigen to be determined and a known quantity of labelled antigen is immunologically reacted in competition with antibody and separated from the remainder of the reaction mixture. The separated labelled antigen bound to the antibody is then quantitated to determine indirectly the total quantity of antigen in the original sample.

A common problem in the foregoing techniques is precise separation of the bound labelled immunological conjugate product from the remainder of the reaction mixture containing unbound labelled material. One technique for such separation is to bind the labelled reaction product to a solid surface which is removed from the liquid reaction mixture. One problem with this technique is the difficulty of measuring certain labels, such as enzymes, on a solid surface because of slow diffusion rates of substrate to enzyme and limited enzyme mobility on the solid surface decreases the collision frequency of enzyme with substrate. The measurement of enzyme activity in the liquid phase is far more rapid and precise. Another disadvantage of this solid phase technique is that the solid phase is not generally capable of regeneration.

One technique for reusing the solid surface and for measuring labelled antigen or antibody in a liquid substrate is set out in Johnson U.S. Pat. No. 3,896,217. There, antibody is irreversibly bound as by covalent bonding to a solid surface followed by immunological reaction with sample antigen and labelling. After separation of the solid surface from the reaction mixture, a cleavage reagent such as ethyl alcohol is added to break the antibody-antigen bond. Subsequently, the thus-freed labelled antigen is measured in the liquid phase and the solid surface is regenerated. Another technique is disclosed in Giaever U.S. Pat. No. 4,041,146 in which an acid is employed as a cleavage reagent between an antibody-antigen bond on a solid surface. These techniques are subject to a number of disadvantages. For example, such cleavage is not effective for total release of the labelled compound. In addition, such cleavage reagents may cause denaturation of enzymes and precipitation of antibodies or antigens.

SUMMARY OF THE INVENTION AND OBJECTS

In accordance with the present invention, a solid phase separation technique is provided for the determination of one or more components of an immunological conjugate in a fluid sample. For simplicity of description, unless otherwise specified, antigen will be designated the sample compound and antibody the corresponding immunological compound of the conjugate. The labelled conjugate is reversibly attached to a solid surface and then released therefrom without the necessity of cleaving immunochemical bonds. In one embodiment, insolubilized sugar is irreversibly bonded to a solid surface and labelled immunological reaction product bonded through antibody to a lectin is selectively and reversibly reactive with the insolubilized sugar. The labelled lectin-bound product is contacted with the specific sugar and retained on the solid surface for separation from the remainder of the reaction mixture including soluble label product. Thereafter, the amount of labelled compound in the insolubilized sugar-bound lectin product is measured as an indication of the quantity of the sample component to be measured. A preferred technique for measurement is to wash the separated labelled product from the column with a solution of sugar of the same type as the labelled product to release the labelled lectin product from the column in solution and thereafter measuring the labelled product in solution.

The above technique is applicable to a rapid flow-through system in which the insolubilized sugar is covalently bonded to a porous particle bed or a solid filter member through which the reaction mixture passes. Also, multiple antigens or antibodies may be analyzed by the use of different specific antibodies or antigens with different labels (e.g., enzymes) in which the reaction mixture is passed through a single column and released therefrom for subsequent analysis of the different enzymes in solution. If desired, the roles of the lectin and sugar may be reversed by insolubilizing the lectin and binding the sugar to one member of the immunological conjugates.

It is an object of the invention to provide an assay for quantitation of one component of an immunological conjugate that overcomes the aforementioned disadvantages of prior art techniques.

It is a specific object of the invention to provide the above type of assay in which the labelled immunological reaction product is separated from the remainder of the reaction mixture by reversible bonding on a solid surface, and thereafter readily released into solution for measurement.

It is a particular object of the invention to provide a specific solid surface immunochemical system utilizing specific lectin-sugar pairs for reversible substrate bonding.

It is another object of the invention to provide a flowthrough system of the foregoing type.

It is a further object of the invention to provide a homogeneous solution incubation procedure followed by the foregoing separation technique.

It is a further object of the invention to provide a system capable of multiple component quantitation.

Further objects and features of the invention will be apparent from the following description in which the preferred embodiments are set forth in detail.

In the immunological method of the present invention the highly specific reversible reaction product of a lectin-sugar pair is employed with one member of the pair in insolubilized form on a solid surface as a mode for separating a labelled immunological reaction product from the immunological reaction mixture. Thereafter, the solid surface may be stripped of the reaction product by passage of soluble sugar or lectin of the same type as is present on the column and the amount of labelled compound in this mixture is determined as a measure of the material to be analyzed.

The present system is applicable to the determination of one component of an immunological conjugate. Broadly stated, such conjugates include any pair of substances which immunologically bind to each other. Specifically, the conjugates include antigens and their antibodies, biologically functional haptens and their antibodies, enzymes and their substrates, hormones and their receptors, and vitamins and their receptors. Thus, they may include a first antibody and a second antibody against the first one. For simplicity of description, unless otherwise specified, the antigen-antibody pair will be designated as the immunological conjugate, with antigen as the component of a fluid sample, specifically serum, to be measured. Other alternatives include analysis for antibody in a sample.

Lectins are proteins or glycoproteins that have receptor sites specificity for a particular sugar or sugars but not for other sugars. For example, Concanvalian A (Con A) has a specificity for alpha-D-glucose and alpha-D-mannose. When a ligand such as glucose is linked covalently to a solid matrix, Con A will be retained on the surface because the glucose ligand will have avidity with Con A's receptor site. This bond is reversible. Thus, a solution of glucose will release the Con A from the surface.

In the present system, the lectin is irreversibly bonded to an antibody or antigen, preferably by known covalent bonding techniques. Such binding is suitably performed by cross-linking the lectin with antigen or antibody through a bifunctional cross-linking agent. Suitable bifunctional compounds are found in the Review by Peters, K. and Richards, F. M. (Ann. Rev. Biochim. 46 (1977) 523). Alkyl imidates show a high degree of specificity among the functional groups presented to them by a protein. The reaction is specific for primary amino groups.

For the determination of antigen in a fluid sample, such as serum, a reaction product is formed including antigen immunologically bound to antibody which is in turn bonded to a lectin. A label compound is included in this reaction product bound to either the same type of antigen or to the same type of antibody in the immunological pair. Then, the reaction product is contacted with insolubilized sugar selectively and reversibly reactive with the bound lectin to reversibly bind the reaction product through the lectin to the insolubilized sugar. Then, the insolubilized sugar-bound lectin reaction product is separated from the remainder of the reaction mixture and the amount of labelled compound in either the reaction product or the remainder is determined as a measure of the quantity of antigen in the sample. Preferably, the label compound in the reaction product is determined and, prior to determination, the insolubilized sugar is contacted with a sugar solution to wash off the lectin product to permit measurement of the label compound in soluble form.

Expressed in a more specific manner, the immunological conjugate reaction product of the previous paragraph is formed as follows. First, the fluid sample containing antigen is contacted with its specific antibody bound to lectin and with a labelled form of either the same antigen or its specific antibody to form an immunological reaction product. The remaining steps are performed as set out above.

The two preferred immunological reaction modes for use with the subject separation system are of the competitive or sandwich type. However, it should be understood that other modes may also be employed so long as the separation is performed using the reversible lectin-sugar bond on a solid surface. The competitive technique will be described first below.

COMPETITIVE HOMOGENEOUS IMMUNOLOGICAL SYSTEM

In one form of the invention, a homogeneous immunological reaction is first performed either sequentially or simultaneously, all in solution. Assuming antigen is to be determined in a fluid sample such as serum, the sample containing antigen is mixed with a known amount of antigen bound to a label compound such as enzyme suitably covalently through a bifunctional cross-linking agent. In addition, the antigen's specific antibody bound to a lectin is added to form a fluid reaction mixture which is incubated. During incubation, the unknown antigen and labelled antigen compete with the lectin-bound antibody in a known manner to form an immunological reaction product. Such product is contacted with insolubilized sugar bound to a solid surface and of a type which is selectively and reversibly reactive with the bound lectin. Bonding of the sugar to solid surface bonding is also suitably of the covalent type through a conventional bifunctional cross-linking agent. The reaction product is reversibly bound through the lectin to the insolubilized sugar.

In the next step, the insolubilized sugar-bound lectin reaction product is separated from the remainder of the reaction mixture. Assuming the substrate comprises a packed column of particles, this step is suitabley performed by flowing the reaction product through the column for removal of the nonlectin portion of the reaction mixture.

Thereafter, the amount of labelled compound in either the insolubilized sugar-bound lectin product or in the remainder of the reaction mixture is determined as a measure of the quantity of antigen in the sample. This step is preferably performed by contacting the insolubilized sugar-bound lectin product with labelled sugar of the same type as the insolubilized sugar to cause the bound lectin product to react with the soluble sugar for conversion to a solubilized form. Then, the soluble and insoluble components are separated into different fractions. Thereafter the amount of labelled compound, preferably in the soluble fraction, is determined as a measure of the quantity of antigen in the sample.

As with a conventional competitive system, in the foregoing enzyme label system, the enzyme concentration in the soluble sugar fraction is derived from an antigen-enzyme conjugate concentration which was in competition with the antigen to be measured for antibody sites and so the enzyme concentration is inversely related to such antigen concentration. A curve may be plotted of enzyme concentration versus incubation time (including subsequent flow through the bed) at various standard concentrations of antigen. From this a second standard curve may be plotted of standard antigen concentration versus enzyme rate at a constant incubation time. The enzyme rate of unknown antigen is measured using the same incubation time. The quantity of unknown antigen may then be determined from the enzyme rate versus antigen plot discussed above.

Certain samples of serum contain glycoprotein which is reactive with the antibody-bound lectin. Such glycoproteins could compete with the insolubilized sugar for the reactive sites of the lectin bound to the labelled immunological conjugate and could cause part of the lectin product to pass through the column without binding to the insolubilized sugar. To avoid this potential source of error, free lectin unbound to antibody and of the same type as the antibody-bound lectin may be added to the sample in excess of the sample glycoprotein reactive with lectin. In this manner, the unbound lectin blocks the lectin-reactive sites of the glycoprotein and removes this source of interference.

In another technique for removing the extraneous glycoprotein interference, prior to contact with the insolubilized sugar, the sample, before or after reaction, may be passed through a bed of insolubilized lectin unbound to antibody and of the same type as the lectin bound to the labelled immunological reaction product. Suitably, the insolubilized lectin is covalently bonded to the bed particles. Passage of the same through this bed causes the glycoprotein to be retained on the column and thereby removed from the sample.

COMPETITIVE FLOWTHROUGH IMMUNOLOGICAL SYSTEM

In this embodiment, no incubation is required prior to contact with the insolubilized sugar. Assuming antigen is to be determined, lectin-bound antibody specific for that antigen is passed through a contained volume such as a porous bed of insolubilized sugar selectively reactive with the bound lectin to reversibly bind the lectin to the insolubilized sugar. The sample containing the antigen and a known amount of antigen in labelled soluble form are passed through the contained volume to cause a competitive immunological reaction between the two forms of antigen for the antibody reactive sites on the column. It is noted that the sample antigen and labelled antigen may be passed through the column simultaneously or in sequence without regard to order of the sequence. Residence time in the bed is regulated to permit completion of the immunological reaction.

The remainder of this assay scheme is the same as that set forth with respect to the homogeneous reaction. Briefly, the portion of the reaction mixture which is not bound through the lectin to the insolubilized sugar is removed from the bed. If desired, this unbound portion may be measured for enzyme activity. Preferably, however, the amount of labelled compound which is bound to the insolubilized sugar is determined as a measure of the quantity of such component in the sample. As set out above, this is preferably performed by stripping the lectin product from the column with a solution of soluble sugar. The same enzyme measurement scheme may be employed using a constant incubation time in the bed for the standard and the unknown. Also as set out above, if the sample contains glycoprotein reactive with the lectin, the glycoprotein reactive sites may be blocked or the glycoprotein removed from the sample in accordance with the foregoing techniques.

The flowthrough competitive technique is particularly adapted to a rapid accurate assay, especially of enzyme, in solution. In one form of the invention, a bed of solubilized lectin is positioned upstream from a bed of the insolubilized sugar. During flowthrough, sample glycoprotein is removed in the first bed while the lectin-immunological reaction product is retained in the second bed. Thereafter, a sugar solution is passed through the second bed to remove the labelled immunological reaction product from the column for analysis.

SANDWICH HOMOGENEOUS IMMUNOLOGICAL SYSTEM

In a typical sandwich technique for the determination of antigen, the antigen is incubated with specific antibody capable of providing means for separation and with other antibody bound to a label compound to form a sandwich of binding solid surface-antibody-antigen-antibody-label compound. In the broad terminology of the present invention, the antigen comprises the one component of an immunological conjugate in the fluid sample, the antibody attached to the binding solid surface comprises the corresponding component of immunological conjugate, while the anti (one component) comprising the antibody bound to a label compound. For simplicity of description, the specific reaction system of solid surface-antibody-antigen-antibody-label will be referred to herein. However, it should be understood that other analogous immunological systems may also be employed such as for detecting antibody in the sample by reversing the roles of the antigen and antibody.

The antigen in the sample is incubated with antibody bound to lectin to cause immunological reaction. Also, such immunologically bound antigen is incubated with labelled antibody to cause a second immunological reaction. These two incubation steps may occur simultaneously, or sequentially in either order so long as the reaction product formed is lectin-antibody-antigen-antibody-label compound, herein the sandwich lectin reaction product.

The sandwich lectin reaction product is then contacted with insolubilized sugar selectively and reversibly reactive with the bound lectin of that product to reversibly bind the lectin to the insolubilized sugar in a similar manner to that set forth above with respect to the competitive homogeneous immunological system. Specifically, the insolubilized sugar-bound lectin reaction product is separated from the remainder of the reaction mixture, and the amount of label compound in the insolubilized sugar-bound lectin product is determined as a measure of the quantity of antigen in the sample. The foregoing techniques of stripping the lectin product from the column with a solution of soluble sugar may also be employed. Also, if the sample contains glycoprotein reactive with the lectin, this source of error may be removed from the system in accordance with the above techniques.

Other systems analogous to the sandwich one may also be used. For example, a lectin-first antibody pair may be incubated with (a) the antigen to be measured which is immunologically reacted with it, as in serum, and (b) a second antibody-label, in which the first antibody is against the second antibody. The antigen which reacts with the first antibody blocks the reactive sites of the first antibody available for reaction with the second one. Thus, the second antibody-label which binds to the first antibody-lectin is inversely related to the amount of antigen and is thus a measure of it. An analogous non-lectin system of this type is the Biotin-Avidin system.

SANDWICH FLOWTHROUGH IMMUNOLOGICAL SYSTEM

As with the competitive flowthrough immunological system, no incubation is required prior to contact with the insolubilized sugar in this technique. Here, the antibody found to lectin is contacted with a contained volume of insolubilized sugar selectively and reversibly reactive with it to reversibly bind the antibody-lectin to the insolubilized sugar. Then, the sample containing antigen is passed through the contained volume under conditions to cause an immunological reaction with the antibody on the column. Thereafter, antibody bound to the label compound is passed through the same column to cause immunological reaction between the antigen on the column and such labelled antibody.

The remainder of the steps are the same as described above with respect to the sandwich homogeneous immunological system. Thus, the insolubilized sugar-bound lectin product is separated from the remainder of the reaction mixture and the amount of label compound is determined as a measure of the quantity of sample component.

DETECTION OF MULTIPLE ANTIGEN OR ANTIBODY

Either the homogeneous or flowthrough, competitive or sandwich, systems are readily adaptable to the detection of two or more antigens or antibodies in a fluid sample such as serum.

In the competitive homogeneous system, two or more antigens or antibodies may be analyzed. A sample containing first and second antigen are mixed and incubated with a known amount of the same first and second antigen bound respectively to different first and second label compounds in soluble form and also with first and second antibodies specific for the sample first and second antigens, respectively, each bound to lectin. The incubated competitive immunological reaction product is then contacted with insolubilized sugar selectively and reversibly reactive with the lectin of that product to reversibly bind the lectin to the insolubilized sugar.

Thereafter, the insolubilized sugar-lectin products are separated from the remainder of the reaction mixture and the amount of first and second label compounds in the insolubilized sugar-lectin products are determined as a measure of the first and second antigens. Such determination is preferably performed by releasing insolubilized sugar-bound lectin product with soluble sugar of the same type as the insolubilized sugar and separating the solution and measuring the amount of first and second label compounds in the soluble fraction. In one embodiment particularly applicable to enzyme labels, the soluble products are separated into different fractions for independent measurement of amounts of first and second different enzymes.

In the sandwich homogeneous system, two or more antigens or antibodies in a fluid sample may be analyzed. For simplicity, a sample containing a first and second antigen will be referred to. This sample is mixed and incubated with a known amount of first and second antigens bound respectively to different first and second label compounds in soluble form. The labelled antigens are of the same type as the first and second sample antigens. Also added to the reaction mixture are first and second antibodies specific for the sample first and second antigens, respectively, each bound to lectin. During incubation, the respective antigen-antibody pairs are formed. This reaction mixture is then contacted with insolubilized sugar selectively and reversibly reactive with the lectin as set out above to reversibly bind the lectin reaction product to the insolubilized sugar. The remainder of the procedure is the same as in the sandwich homogeneous system.

The competitive flowthrough system is also applicable to the determination of multiple antigens and antibodies in the sample. In a specific embodiment, the first and second antibodies specifically reactive with the first and second antigen and bound to a lectin are passed through a contained volume of insolubilized sugar selectively and reversibly reactive with bound lectin. In this manner, the lectin-antibody is specifically bound to the solubilized sugar. Then, sample containing the first and second antigen and a known amount of labelled first and second antigens in soluble form are passed through the contained volume to cause the competitive immunological reaction between the labelled and unlabelled antigens for the sugar-bound antibodies.

The remainder of the competitive flowthrough procedure for analysis of multiple antigens is set forth above. Briefly, the reaction mixture which does not bind to the insolubilized sugar substrate is removed from the contained volume of insolubilized sugar. Then, the amount of first and second labelled compounds in the unsolubilized sugar-bound lectin product solid surface is determined as a measure of the first and second antigen in the sample. Preferably, the lectin products are stripped from the insolubilized sugar substrate by passage of a sugar solution and the soluble portion is separated for analysis of the labelled compounds.

The sandwich flowthrough system may also be employed for the analysis of multiple antigens or antibodies. The following description refers to the analysis of first and second antigens in a sample. First and second antibodies specific to the sample first and second antigens, respectively, and bound to lectin, pass through a contained volume of insolubilized sugar which reversibly binds the lectin-antibody to the insolubilized sugar. Then, the sample containing first and second antigen are passed through the contained volume to cause immunological reaction to occur with the sugar bound antibodies. Thereafter, third and fourth antibodies to the sample antigens bound to first and second labelled compounds, respectively, are passed through the contained volume of sugar to cause immunological reaction with the first and second sample antigens. Thereafter, the reaction mixture is not bound through the lectin to the insolubilized sugar is separated and the amount of first and second labelled compounds on the insolubilized sugar-bound lectin product is determined as a measure of the quantity of the first and second antigen in the sample.

Although the preferred system is for the sugar to be insolubilized on a solid surface and used for separation while the lectin is integrated into the immunological reaction product, it should be understood that the roles of the lectin and sugar may be reversed, if desired, for the particular technique. In that event, the lectin is preferably insolubilized by conventional techniques such as covalent bonding through the combined functional coupling reagent. The same coupling technique may also be employed for binding the sugar to the antigen or antibody.

LECTIN-SUGAR PAIRS

As set out above, the reversible sugar-lectin bond provides the mode of separation of the immunological reaction product in all of the foregoing techniques. The highly specific nature of the lectin-sugar bond renders the system particularly useful. A sample list of lectins and specific sugars are set out below.

TABLE I

| Lectin | Sugar |
| --- | --- |
| *Arachis Hypogaea Agglutinin* (PNA) | D-Gal $\beta$ (1→3)-GalNAc |
| *Bauhinia Purpurea Agglutinin* (BPA) | D-GalNAc, D-Gal |
| *Bendeirea Simplicifolia Agglutinin* (BSA) | $\alpha$-D-Gal |
| *Canavalia Ensoformis Agglutinin* (CON A) | $\alpha$-D-Man, $\alpha$-D-Glc. |
| *Dolichos Biflorus Agglutini* (DBA) | $\alpha$-D-GalNAc |
| *Glycine Max* (SBA) | D-Gal, $\alpha$-D-GalNAc |
| *Lens Culinaris* (LcH) | $\alpha$-D-Man, $\alpha$-D-Glc |
| *Limulus Polyhemus* (LPA) | Sialic Acid |
| *Lotus Tetragonolobus* (Lotus A) | $\alpha$-L-Fucose |
| *Phaseolus Vulgaris* (L-PHA) | D-GalNAc |
| *Phaseolus Limensis* (LBA I) | $\alpha$-D-GalNAc |
| *Phaseolus Vulgaris* (H-PHA) | D-GalNAc |
| *Pisum Sativum* (PEA) | $\alpha$-D-Man, $\alpha$-D-Glc. |
| *Phytolacca Americana* (Pokeweed) | |
| *Ricinus Communis* (RCA I) | $\beta$-D-Gal |
| *Ricinus Comunis* (RCA II) | $\beta$-D-Gal, D-GalNAc |
| *Sophora Japonica* (SJA) | $\alpha$-D-GalNAc |
| *Triticum Vulgaris* (WGA) | ($\beta$(1→4)-D-GlcNAc)2 (Sialic Acid) |
| *Ulex Europeus* (UEA I) | $\alpha$-L-Fucose |
| *Ulex Europaeus* (UEA II) | (D-GlacNAc)2 |
| *Wisteria Floribunda* (WFA) | D-GalNAc |

It should be understood that isomers of the foregoing lectins may also be employed in accordance with the scope of the present invention.

The foregoing lectins are firmly bound to the appropriate immunological substance, (e.g., antibody, antigen or haptens), through a bifunctional reagent. Any of these substances which form immunological conjugates may be employed in the present invention. Exemplary antigens are as follows.

TABLE II

Albumin
2 H-Globulin
Cancinoembryonic antigen
Choriogonadotropein
Heptoglobulin
Hepatitis B surface antigen
IgE
IgG
IgM
Insulin
Placental Lactogen
Pregnancy-associated macroglobulin
Virbio Cholerae-exotoxin lipopolysaccharide Exemplary haptens are as follows:

TABLE III

Cortisol
Estrogens
2,4-Dinitrophenol
Progesterone
1 Thyrotropin
Morphine & other opiates
Amphetamine
Barbituate
Methadone
Benzoyl ecogonine
(Cocaine metabolite)
Diphenylhydantoin
Phenobarbital

TABLE III-continued

Primidone
Digoxin
Morphine and Codeine
Thyroxine

By way of example, antibodies against the antigens in the following table may be employed.

TABLE IV

Amoeba, strain HK-g
Albumin, serum
Allergens, various
Carcinoembryonic antigen
choriogonadotropin
DNA
human IgG, IgM, IgA
Dextran
2,4-dimtrophenol
*Echinococcus granulous*
*E. Coli* enterotoxin
o and kl antigens
$\alpha$-Fetoprotein
$\gamma$-Globulin
IgG myeloma proteins
Immunologlobulin light chains
Hog cholera virus
*Onchocera volualus*
Plosmodium species
Rubella Virus
Salmonella species, O antigens
*Schistosoma mansoni*
Streptolysin O
Toxoplasma Gondiu
*Trichinella spiralis*
*Trypanosoma Cruzi*
*Trypanosoma rhodescense* and
*Trypanosoma Brucei*
*Vibrio choterae*, exotoxin
and liposaccharide In the present system, strong bonds are required among the following pairs and substances (a) lectin and with the one compound of the immunological conjugate (e.g., antigen, antibody or hapten), (b) label compound with such one component, and (c) sugar with the insolubilizing substrate. Similar bifunctional reagents may be employed to couple these compounds as set out in the aforementioned Review by Peters and Richards. Such coupling reagents include amidoesters such as dimethyl malonimidate, azides such as the acryl azide of tartryl diazide which reacts readily with immuno groups to produce amidelinkages. Aryl dihalides (e.g., 1,5-difluoro-2,4,-dinitrobenzene, or 4,4'-difluoro-3,3'-dinitrophenyl sulfone, glutaraldehyde, 1-ethyl-3-(3-dimethylaminopropyl) carbodiimide hydrochloride, dimaleinide, mixed anhydride, mixed anhydride, m-maleamidobenzylboyl N-hydroxysucciinimide ester, and other known cross-linking agents.

All of the foregoing bonds are essentially irreversible. In addition, bifunctional reagents with functional groups such as disulfide or glycol may be used. Such bonds can be broken after the cross-linking reaction. Such reagents include dimethyl 3,3'-dithiobispropionimidate, sussinimidyl propionimidate, N-(3-Fluoro-4,6-dinitrophenyl)-cystamine, tartryl diazide, tartryl di(glycylazide) and tartryl di($\epsilon$-amino caproylazide).

In some instances, the bonds may be formed directly between the reagents themselves. For example, antibody and enzymes can be linked through functional groups on the respective materials. As a specific example, horseradish peroxidase containing carbohydrate may be treated with periodate and reacted with antibody to give a Schiff base formation without inhibiting its enzyme activity or blocking immunological activity of the antibody.

Known techniques using bifunctional cross-linking agents in conventional enzyme immunoassays include the following (a) a one-step glutaraldehyde linkage (Avrameas, S. Immunochemistry 6 (1969) 43), (b) two-step glutaraldehyde linkage (Avrameas, S. Immunochemistry (1971) 1175), (c) oxidation of saccharide residues and Schiff base formation (Nakane, P. K., J. Hisothem. Cytochem. 22 (1974) 1084), and (d) Dimaleimide linkage (Kato, K., et al, Euro. J. Biochem. 62, (1966) 285).

The solid phase surface for insolubilizing the sugar or lectin of the present invention is preferably of a porous character which permits solutions to pass through the same. Thus, for example, the solids of cellulose filter paper bed may be employed. More preferably, particulate beads are employed which provide less resistance to flow. Such beads may be formed of glass, polystyrene, sheet polyacrylamide gel, nylon-6, agarose, or any other material capable of forming a covalent bond with the sugar or lectin to be employed in the separation step of the present invention.

Any conventional label which can be firmly attached to an immunological substance (e.g., antigen, antibody or hapten) may be employed in the present invention. Such labels include a luminescent substance, such as a phosphor or a fluorogen, a bioluminescent substance, a radioactive substance, an enzyme, spin labels, or a metal containing substance. As set out above, the preferred label is an enzyme.

Suitable fluorescent labels include lissanime rhodamine B, D.A.N.S. (1-dimethlyamino-naphthalene-5-sulfonic acid), ortho-phthaldehyde, fluorescein isothiocyanate and fluorescamine, which are frequently used in fluorescence microscopy.

Any of a number of known enzyme label systems may also be employed. One system is described in an article by Pesce et al entitled "Use of Enzyme-Linked Antibodies to Measure Serum Anti-DNA Antibody in Systemic Lupus Erthyematosus", Clin. Chem. 20/3, 353-359 (1974). Another is described in Wisdom, G. B., Clin. Chem. 22, (1976) 1243. A list of suitable enzymes may be found in Hawk, et al, Practical Physiological Chemistry, McGraw-Hill Book Company, New York (1954) page 306-397. The following is a list of suitable classes of enzymes and specific enzyme examples:

TABLE V

| Class | Enzyme Example |
|---|---|
| Hydrolases Carbohydroases | Amylases |
| Nucleases | Polynuceotidase |
| Amidases | Arginase |
| Purine deaminases | Adenase |
| Peptidases | Aminopolypeptidase |
| Proteinases | Pepsin |
| Esterases | Lipases |
| Iron Enzymes | Catalase |
| Copper Enzymes | Tyrosinases |
| Enzymes containing Coenzymes | Alcohol dehydrogenase |
| Enzymes reduced cytochrome | Succinic dehydrogenase |
| Yellow enzymes | Diaphorase |
| Mutases | Glyoxalase |
| Demolases | Aldolase |
| Other enzymes | phosphorylases |
| | Hexokinases |

The concentration of enzyme is determined by comparison with a standard curve, just like other labels such as fluorecent and radioactive ones.

A further disclosure of the nature of the present invention is provided by the following specific examples of the practice of the invention. It should be understood that the data disclosed serve only as examples and are not intended to limit the scope of the invention.

EXAMPLE 1

PREPARATION OF LECTIN-ANTIBODY PAIR (ONE STEP)

5 mg. of purified PNA (lectin) is dissolved in 1 ml of buffer solution containing 0.1 M lactose, 0.1 M phosphate buffer pH 7.2, 0.15 M sodium chloride, and 5 mg of goat anti-human IgG antibodies, and 10–20 microliter of a coupling agent (lambda redistilled glutaraldehyde) is added. This mixture is incubated for one hour at room temperature. Dialysis against 1 liter 0.1 M phosphate buffered saline. Then it is passed through a galactose (1–3) galactosamine linked agarose beads column having specificity to retain PNA and PNA-antibodies on the column matrix. The column is washed until the $OD^{280}$ measurement is 0.050. Then, the PNA complex is eluted from the column by using a specific sugar such as 0.5 M lactose solution and then passed through a second column containing human IgG coupled agarose beads. The PNA-antibodies are dissociated from the matrix by using either 0.1 M acetic acid. (Or 3 M sodium isothiocyanate or other reagents.) The complex is extensively dialyzed against phosphate buffer saline. The eluted solution is concentrated and passed through a gel filtration column which separates constituents by molecular weight. The fraction is collected which corresponds to a molecular weight of a lectin-antibody pair in a one to one conjugation ratio.

EXAMPLE 2

(TWO STEP METHOD FOR PREPARING LECTIN-ANTIBODY PAIR)

To one ml of phosphate buffer saline pH 7.2 containing one mg PNA mixed with two ml of galactose (1–3) galactosamine linked agarose beads matrix specific for PNA binding. Glutaraldehyde is added and the mixture is incubated for 1–6 hours. The gel is washed on a sintered glass filter funnel with PBS. This gel is suspended in a solution of 1 mg of goat anti-human IgG antibodies overnight. The beads are washed with PBS and then washed with 0.1 M specific sugar solution to release lectin-antibody complexes from the matrix. The eluant is collected and passed through a column containing human IgG coupled agarose beads. The rest of the procedure is the same as for Example 1.

EXAMPLE 3

DIRECT APPLICATION OF ENZYME LECTIN TO MEASURE GLYCOPROTEIN, OR POLYSACCHARIDES, OR GLYCOLIPID

To antibody coated polystyrene tube are added a series of known concentration of human IgG from 0.001 ng to 1 μg in one ml of 0.1 M phosphate buffer saline pH 7.2 containing human serum albumin. This mixture is incubated at 40° C. for one hour, decanted and washed with phosphate buffer saline. To each tube is added 1 ml of lectin-enzyme (10 μg/ml) such as WGA-horseradish peroxidase or Con A-microperoxidase or other lectin-enzyme conjugates. This is incubated for two hours, decanted and washed with phosphate buffer saline with 0.01% Tween 20. To the empty tube 0.01% hydrogen peroxide and O-dianisdine are added and incubation proceeds for 15 minutes. The O.D. at 465 mu is recorded. The same procedure is used for the unknown.

EXAMPLE 4

MULTIPLE TESTS

A series of known concentration human IgG and IgM from the range of 100 ng to 20 μg is prepared. To each tube containing the known, are added 30 μg of PNA-anti IgG and PNA-anti IgM and 10 ng human IgG-alkaline phosphatase and 10 ng human IgM-horseradish peroxidase are added.

Incubation proceeds for one hour. This mixture is transferred to a column containing a filter disc or matrix coated with sugar specific for PNA. Then the column is washed with 2×4 ml phosphate buffered saline containing 0.01% Tween 20 and the eluant is collected. One ml of eluant is tested to determine the horseradish peroxidase activity after incubating with 0.01% hydrogen peroxide and O-dianisidine. Another ml is tested to determine the alkaline phosphatase activity by incubating with 0.001 M p-nitrophenyl phosphate in 0.1 M sodium carbonate buffer pH 10.0. A standard curve of concentration against optical density thus is obtained. However, when IgG or IgM concentration of a human serum is to be determined, the same enzymes in the human serum would cause interference. So an alternative route is provided. The PNA-antibody-IgG-enzyme complexes are eluted from the column disc with a solution of 0.1 M specific sugar solution. The activity of the enzymes are determined to form a standard curve. The same procedure is followed for the unknown, and its concentration can be obtained from the curve for the IgG and IgM.

EXAMPLE 5

TESTING THYROXINE AND THYROID STIMULATING HORMONE (TSH) BY SIMULTANEOUS MULTIPLE ENZYME IMMUNO-TEST

A. Thyroxine-horseradish peroxidase conjugates are prepared by a double labelling technique. 1 mg thyroxide hydrochloride is ethanol-0.1 M bicarbonate buffer solution pH 8.0 with radioisotope $I^{125}$ labelled thyroxine ($2\times 1-^6$ cpm) is mixed with 1 mg horseradish peroxidase (HRP) by Nakane's procedure. (Nakane, P. Q., and Kawavi, A. J., Histochem. Cytochem. 22, 1084 (1974). The conjugate is formed after overnight incubation at 4° C. Then the mixture is dialyzed against 0.1 M phosphate buffer saline three times. The conjugates are further purified by passing through a Sephadex column G-200 (2 cm×. 75 cm) and DEAE Sepharose column. The concentration of HRP is measured and the cpm of the total dialysate is determined. Thus, the number of thyroxide molecules per molecule of HRP can be deduced. A plot of the concentration of HRP against the rate of the peroxidase is drawn based on the optical density increase or fluorescent signals at absorbance 465 mu per unit time at various enzyme concentrations when hydrogen peroxide and O-dianisidine are used.

Thyroid stimulating hormone (TSH) or Thyrotropinaalkaline phosphate conjugates are prepared.

500 μg TSH is mixed with 2 mg alkaline phosphatase at pH 8.0–1.0 M bicarbonate buffer and 20 microliter glutaraldehyde. This mixture is incubated overnight at 4° C. and then dialysed against 0.1 M phosphate buffered saline extensively. The dialysate is passed through a Sephadex G-200 column (2 cm×. 75 cm) or Ultragel 34 column to separate the conjugates from the non-conjugates. The concentration of the conjugate is determined by Lowry's method. Concentration of the conjugate against the rate of enzyme reaction is plotted by measuring the absorbance at 405 mu increment per unit time at various enzyme concentrations when p-nitrophenyl phosphate at 0.001 M concentration in carbonate buffer—0.1 M pH 10 is used as the substrate.

B. STANDARD PLOT OF THYROXINE IN HUMAN SERUM

To a human serum free of thyroxine and TSH (100 microliter), the following are added: 300 microliter 0.1 M phosphate buffered saline pH 7.2, thyroxine concentration varying from 2 ng to 100 ng per 100 microliter, 1 ng thyroxine-HRP conjugate, 100 ng PNA-anti-T$_4$, 1 ng TSH-alkaline phosphatase, various known concentration TSH and 100 ng PNA-anti-TSH.

The 500 microliter is incubated at 37° C. for 30 minutes. Then it is transferred onto the galactose-$\beta$ (1→3) galactosamine conjugate agarose beads (exclusion limit 1.5 M to 15 M) bed volume 1 ml. The column is washed with 4 ml of PBS and then washed with 2 ml 0.5 M lactose PBS solution and this eluant is collected. The enzyme activity of HRP per 0.5 ml lactose eluant is assayed. The rate of HRP reaction is plotted against the known concentration of thyroxine added. The alkaline phosphatase activity is then plotted against the known concentration of TSH added.

C. TESTING THE UNKNOWN CONCENTRATION OF THYROXINE AND TSH BY SIMULTANEOUS MULTIPLE ENZYME IMMUNO TEST

To each 100 microliter of unknown sample, add 300 microliter 0.1 M phosphate buffered saline pH 7.2, 100 ng PNA-anti-T$_4$, 100 ng PNA-anti-TSH, 1 ng HRP-T$_4$ and 1 ng TSH-alkaline phosphatase. The mixture is incubated and treated as is the standard in part B.

From the enzyme activity detected from unknown sample, the concentration of thyroxine and thyroid stimulating hormone is located on the standard plot.

EXAMPLE 6

ALTERNATE FLOW THROUGH METHOD

1. Incubate 1 ml galactose $\beta$ (1→3)-Galactosamine conjugated matrix column with 500 ng PNA conjugated T$_4$ antibody and TSH antibody.
2. Wash with 0.1 M phosphate buffered saline.
3. Mix with 1 ng each of T$_4$-HRP and TSH-alkaline phosphatase, 300 microliter PBS with 100 microliter serum and without serum for 5 minutes at room temperature.
4. Transfer to the column and collect the eluant and wash with 3 ml of 0.1 M phosphate buffered saline pH 7.2.
5. Wash the column with two ml of 0.5 m lactose containing PBS.
6. Collect the eluant.
7. Take 0.5 ml of eluant for enzyme assay using O-dianisidine for T$_4$-horseradish peroxidase conjugate, and 4-methylmbelliferone phosphate for alkaline phosphate, and record rate of reaction.

EXAMPLE 7

SANDWICH HOMOGENEOUS IMMUNOLOGICAL SYSTEM

To a test tube are mixed (1) 0.5 ml human serum (2) 0.1 ml lectin solution containing 20 μg PNA, (3) 0.1 ml containing 10 μg purified to PNA to rabbit anti-human insulin antibody conjugates, (4) 0.1 ml containing 1 μg Alkaline Phosphotase to goat anti-human insulin antibody conjugates, and (5) 0.2 ml 0.1 M phosphate buffered saline pH 7.2. The mixture is incubated for 30 minutes at 37° C.

After incubation, the mixture is directed through a column containing Galactose-$\beta(1\rightarrow3)$ N-Acetyl-Galactosamine (herein Gal$\beta$ (1$\rightarrow$3) GalNac) linked agarose beads or solid matrix. Then the solid matrix is washed with 5 ml phosphate buffered saline. 4 ml 0.2 M (Gal$\beta$ (1$\rightarrow$3) GalNac phosphate buffered saline is then added. The eluent is collected and the alkaline phosphatase activity is assayed. From a standard curve, based on different known concentrations of insulin against enzyme activities, the concentrate of insulin based on the determined enzyme activity is located. The standard curve is formed with known concentrations of insulin instead of human serum.

What is claimed is:

1. A method for the determination of one component of an immunological conjugate in a fluid sample comprising the steps of
    (a) forming an immunological conjugate reaction product including said one component from a fluid sample immunologically bound to its corresponding component, a bound label compound, and a bound lectin, said lectin being bound to said corresponding component,
    (b) contacting said reaction product with insolubilized sugar selectively and reversibly reactive with said bound lectin to reversibly bind the reaction product through the lectin to the insolubilized sugar,
    (c) separating the insolubilized sugar-bound lectin product from the remainder of said reaction mixture, and
    (d) determining the amount of label compound in either said insolubilized sugar-bound lectin product or said remainder as a measure of the quantity of said one component in said sample.

2. A method for the determination of one component of an immunological conjugate in a fluid sample comprising the steps of
    (a) contacting fluid sample containing said one component with its corresponding immunological component bound to a lectin and with a labelled or an anti(corresponding component) to form an immunological reaction product,
    (b) incubating the reaction mixture of step (a) for a sufficient time to cause an immunological reaction,
    (c) contacting said incubated reaction mixture with insolubilized sugar selectively and reversibly reactive with said bound lectin to reversibly bind the lectin to the insolubilized sugar, and
    (d) separating the insolubilized sugar-bound lectin reaction product from the remainder of said reaction mixture.

3. A method for the determination of one component of an immunological conjugate in a fluid sample comprising
    (a) mixing said sample containing said one component with a known amount of said one component bound to a label compound in soluble form and with the corresponding component of said immunological conjugate bound to a lectin to form a fluid reaction mixture,
    (b) incubating the reaction mixture of step (a) to cause a competitive immunological reaction,
    (c) contacting said incubated reaction mixture with insolubilized sugar selectively and reversibly reactive with said bound lectin to reversibly bind the lectin to the insolubilized sugar,
    (d) separating the insolubilized sugar-bound lectin reaction product from the remainder of said reaction mixture, and
    (e) determining the amount of label compound in either said insolubilized sugar-bound lectin product or said remainder as a measure of the quantity of said one component in said sample.

4. The method of claim 3 in which said one component of said immunological conjugate is selected from the group consisting of antigen, antibody, or portions and equivalents thereof.

5. The method of claim 4 in which said one component is an antigen and said corresponding component is an antibody.

6. The method of claim 3 in which said one component is an antibody and said corresponding component is an antigen.

7. The method of claim 3 in which said label compound is selected from the group consisting of enzyme, radioactive molecules, and fluorescent molecules.

8. The method of claim 7 in which said label compound is an enzyme and the amount of said enzyme is determined by measuring its enzyme activity.

9. The method of claim 3 in which step (e) is performed by contacting said insolubilized sugar-bound lectin product with soluble sugar of the same type as said insolubilized sugar to cause the bound lectin product to react with said soluble sugar for conversion to a solubilized form, then separating the soluble and insoluble components into different fractions and thereafter measuring the amount of label compound in the soluble fraction.

10. The method of claim 3 in which the insolubilized sugar comprises sugar covalently bound to a solid surface.

11. The method of claim 3 in which said sample contains glycoprotein reactive with lectin and prior to step (c) said unbound lectin is added to said sample of the same type as said bound lectin, said unbound lectin being in excess of said glycoprotein reactive therewith in the sample, so that said unbound lectin blocks the lectin-reactive sites of said glycoprotein.

12. The method of claim 3 in which said sample contains glycoprotein reactive with lectin and prior to step (c) said sample is passed through a bed of insolubilized lectin with glycoprotein-reactive sites and of the same type as said bound lectin so that said glycoprotein is retained on said column and thereby removed from said sample.

8. Find the concentration of conjugates from a standard curve after subtracting the bank.

9. Find the concentrate of T$_4$ and TSH of an unknown from a known concentration of T$_4$, and TSH.

13. A method for the determination of one component of an immunological conjugate in a fluid sample comprising the steps of
(a) incubating said sample containing said one component with the corresponding component of said immunological conjugate bound to a lectin to cause said immunological reaction to occur,
(b) incubating the one component with anti(one component) bound to a label compound to cause an immunological reaction between said one component and said anti(one component),
(c) contacting the reaction mixture of step (b) with insolubilized sugar selectively and reversibly reactive with said bound lectin to reversibly bind the lectin to the insolubilized sugar,
(d) separating the insolubilized sugar-bound lectin reaction product from the remainder of said reaction mixture, and
(e) determining the amount of label compound in either said insolubilized sugar-bound lectin product or said remainder as a measure of the quantity of said sample component.

14. The method of claim 13 in which said one component is an antigen and said corresponding component and anti(one component) are different antibodies immunologically reactive with said antigen.

15. A method for the determination of at least a first and second antigen or antibody in a fluid sample comprising
(a) mixing and incubating said sample containing said first and second antigens (or antibodies) with (1) a known amount of said first soluble antigen (or antibody) bound to a first label compound and a soluble second antigen (or antibody) bound to a different second label compound and (2) first and second antibodies (or antigens) specific for the sample first and second antigens (or antibodies), respectively, and bound to lectin to form the respective antigen-antibody pairs,
(b) contacting said incubation reaction mixture with insolubilized sugar selectively and reversibly reactive with said lectin to reversibly bind the lectin to the insolubilized sugar,
(c) separating the insolubilized sugar-lectin products from the remainder of said reaction mixture, and
(d) determining the amount of first and second label compounds in either said insolubilized sugar-lectin products of said remainder as a measure of the quantity of said first and second antigens.

16. The method of claim 15 in which step (d) is performed by contacting said insolubilized sugar-bound lectin products with soluble sugars of the same type as said insolubilized sugar to cause the bound lectin products to react with said soluble sugar for conversion to a solubilized form, then separating the soluble and insoluble components into different fractions and thereafter measuring the amount of first and second label compound in the soluble fraction.

17. The method of claim 15 in which the insolubilized sugar is covalently bound to a solid surface.

18. The method of claim 15 in which prior to step (d), the sugar-lectin products are separated into different fractions for independent measurement of the amounts of first and second labels.

19. A method for the determination of at least a first and second antigen or antibody in a fluid sample comprising the steps of (a) incubating said sample containing said first and second antigens or antibodies with first and second antibody or antigen, specific for said sample antigens or antibodies, and bound to lectins to form the respective antigen-antibody pairs,
(b) incubating the reaction product of step (a) with a third antibody or antigen bound to a first label component and a fourth antibody or antigen bound to a second label compound to cause said third and fourth antibodies ot antigens to immunologically react with said first and second sample antigens or antibodies,
(c) contacting the reaction mixture of step (b) with insolubilized sugar selectively and reversibly reactive respectively with said lectin to reversibly bind the lectin to the insolubilized sugar,
(d) separating the insolubilized sugar-lectin products from the remainder of said reaction mixture, and
(e) determining the amount of first and second label compounds in either said insolubilized sugar-lectin product or said remainder as a measure of the quantity of said first and second antigens.

20. The method of claim 19 in which prior to step (e) the sugar-lectin products are separated into different fractions for independent measurement of the amounts of first and second labels.

21. The method of claim 19 in which step (e) is performed by contacting said insolubilized sugar-lectin product with soluble sugar of the same type as said insolubilized sugar to convert the lectin product to solubilized form, separating the soluble and insoluble components into different fractions, and thereafter measuring the first and second label compounds in the soluble fraction.

22. A method for the determination of one component of an immunological conjugate in a fluid sample, comprising the steps of
(a) passing the corresponding component of said immunological conjugate bound to a lectin through a contained volume of insolubilized sugar selectively and reversibly reactive with said bound lectin to reversibly bind the corresponding component bound lectin to the insolubilized sugar,
(b) passing said sample containing said one component and a known amount of said one component bound to a label compound in soluble form through said contained volume to cause a competitive immunological reaction between the components of said immunological conjugate,
(c) separating the insolubilized sugar-bound lectin reaction product from the remainder of said reaction mixture, and
(d) determining the amount of label compound in said insolubilized sugar-bound lectin product as a measure of the quantity of said one component in said sample.

23. The method of claim 22 in which step (d) is performed by contacting said insolubilized sugar-bound lectin product with soluble sugar of the same type as said insolubilized sugar to cause the bound lectin product to convert to a solubilized form, separating the soluble and insoluble components into different fractions and thereafter measuring the amount of label compound in the soluble fraction.

24. The method of claim 22 in which said sample contains glycoprotein reactive with lectin and lectin unbound to said corresponding component and of the same type as said bound lectin is present in said sample during step (b) said unbound lectin being in excess of glycoprotein reactive therewith in the sample, so that said unbound lectin blocks the lectin-reactive sites of said glycoprotein.

25. The method of claim 22 in which said sample contains glycoprotein reactive with lectin and prior to step (b) said sample is passed through a bed of insolubilized lectin with glycoprotein-reactive sites and of the same type as said bound lectin so that said glycoprotein is retained on said column and thereby removed from said sample.

26. A method for the determination of one component of an immunological conjugate in a fluid sample, comprising the steps of
  (a) contacting the corresponding component of said immunological conjugate bound to a lectin with a contained volume of insolubilized sugar selectively and reversibly reactive with said bound lectin to reversibly bind the lectin to said insolubilized sugar,
  (b) passing said sample containing said one component through said contained volume under conditions to cause immunological reaction with said corresponding component,
  (c) passing anti(one component) bound to a label compound through said contained volume to cause an immunological reaction between said one component and said anti(one component),
  (d) separating the insolubilized sugar-bound lectin reaction product from the remainder of said reaction mixture, and
  (e) determining the amount of label compound in said insolubilized sugar-bound lectin product as a measure of the quantity of said sample component.

27. The method of claim 26 in which said sample contains glycoprotein reactive with lectin and lectin unbound to said corresponding component and of the same type as said bound lectin is present in said sample during step (b), said unbound lectin being in excess of glycoprotein reactive therewith in the sample, so that said unbound lectin blocks the lectin-reactive sites of said glycoprotein.

28. The method of claim 26 in which said sample contains glycoprotein reactive with lectin and prior to step (b) said sample is passed through a bed of insolubilized lectin with glycoprotein reactive sites and of the same type as said bound lectin so that said glycoprotein is retained on said column and thereby removed from said sample.

29. A method for the determination of one component of an immunological conjugate in a fluid sample, comprising the steps of
  (a) passing the corresponding component of said immunological conjugate bound to sugar through a contained volume of insolubilized lectin selectively and reversibly reactive with said bound sugar to reversibly bind the sugar to the insolubilized sugar,
  (b) passing said sample containing said one component and a known amount of said one component bound to a label compound in soluble form through said contained volume to cause an immunological reaction between the components of said immunological conjugate,
  (c) separating the insolubilized lectin-bound reaction product from the remainder of said reaction mixture, and
  (d) determining the amount of label compound in said insolubilized sugar-bound lectin product as a measure of the quantity of said one component in said sample.

30. The method of claim 26 in which step (d) is performed by contacting said insolubilized lectin-bound sugar product with soluble lectin of the same type as said insolubilized lectin to cause the bound sugar product to convert to soluble form, then separating the soluble and insoluble components into different fractions and thereafter measuring the amount of label compound in the soluble fraction.

31. A method for the determination of one component of an immunological conjugate in a fluid sample, comprising the steps of
  (a) contacting the corresponding component of said immunological conjugate bound to a sugar with a contained volume of insolubilized lectin selectively and reversibly reactive with said bound sugar to reversibly bind the sugar to said insolubilized lectin,
  (b) passing said sample containing said one component through said contained volume to cause said immunological reaction to occur,
  (c) passing anti(one component) bound to a label compound through said contained volume to cause an immunological reaction between said one component and said corresponding component,
  (d) separating the insolubilized sugar-bound lectin reaction product from the remainder of said reaction mixture, and
  (e) determining the amount of label compound in said insolubilized sugar-bound lectin product as a measure of the quantity of said sample component.

32. The method of claim 31 in which during step (b) said sample contains lectin unbound to said corresponding component and of the same type as said bound lectin in excess of extraneous glycoprotein reactive in the sample so that at least a portion of said unbound lectin blocks said lectin reactive sites of said glycoprotein.

33. A method for the determination of one component of an immunological conjugate in a fluid sample comprising
  (a) mixing said sample containing said one component with a known amount of said one component bound to a label compound in soluble form, and the corresponding component of said immunological conjugate bound to a sugar to form a fluid reaction mixture,
  (b) incubating the reaction mixture of step (a) to cause an immunological reaction between the components of said immunological conjugate,
  (c) contacting said incubated reaction mixture with insolubilized lectin selectively and reversibly reactive with said bound sugar to reversibly bind the sugar to the unsolubilized lectin,
  (d) separating the insolubilized lectin-bound sugar reaction product from the remainder of said reaction mixture, and
  (e) determining the amount of label compound in said insolubilized lectin-bound sugar product as a measure of the quantity of said one component in said sample.

34. The method of claim 33 in which the insolubilized lectin comprises lectin covalently bound to a solid surface.

35. A method for the determination of one component of an immunological conjugate in a fluid sample comprising the steps of (a) incubating said sample containing said one component with the corresponding component of said immunological conjugate bound to a sugar to cause said immunological reaction to occur, (b) incubating the reaction product of step (a) with anti(one component) bound to a label compound to cause an immunological reaction between said one component and said anti(one component), (c) contacting the reaction mixture of step (b) with insolubilized lectin selectively and reversibly reactive with said bound sugar to reversibly bind the sugar to the insolubilized lectin, (d) separating the insolubilized lectin-bound sugar reaction product from the remainder of said reaction mixture, and (e) determining the amount of label compound in said insolubilized lectin-bound sugar product as a measure of the quantity of said sample component.

36. The method of claim 35 in which said immunological conjugate is an antigen-antibody pair.

37. The method of claim 36 in which said one component is an antigen and said corresponding component and anti(one component) are different antibodies immunologically reactive with said antigen.

38. A method for the determination of at least first and second antigens or antibodies in a fluid sample, comprising the steps of (a) passing through a contained volume of insolubilized sugar, first and second antibodies or antigens specific for the sample first and second antigens or antibodies, respectively, each specific antibody or antigen being bound to a lectin, said sugar being selectively and reversibly reactive with said bound lectin, to reversibly bind the lectin to the insolubilized sugar, (b) passing said sample containing said first and second antigens or antibodies and a known amount of said first and second antigens or antibodies bound respectively to first and second label compounds in soluble form through said contained volume to cause an immunological reaction between the first and second antigens or antibodies and said first and second sugar-bound antibodies or antigens, respectively, (c) separating the insolubilized sugar-bound lectin reaction products from the remainder of said reaction mixture, and (d) determining the amount of first and second label compounds in said insolubilized sugar-bound lectin products as a measure of the of said first and second antigens or antibodies in said sample.

39. The method of claim 38 in which step (d) is performed by contacting said insolubilized sugar-bound lectin products with soluble sugar of the same type as said insolubilized sugar to cause the bound lectin products to react with said soluble sugar for conversion to a solubilized form, separating the soluble and insoluble components into different fractions and thereafter measuring the amount of first and second label compound in the soluble fraction.

40. A method for the determination of at least a first and second antigen or antibody in a fluid sample, comprising the steps of (a) passing through a contained volume of insolubilized sugar, first and second antibodies or antigens, specific for said sample first and second antigens, respectively, each antibody or antigen being bound to lectin, said insolubilized sugar being selectively and reversibly reactive with said bound lectin to reversibly bind the lectin to said insolubilized sugar, (b) passing said sample containing said first and second antigens or antibodies through said contained volume to cause an immunological reaction to occur with said first and second sugar-bound antibodies or antigens, (c) passing third and fourth antibodies to said sample antigens or antibodies bound to first and second label compounds, respectively, through contained volume to cause an immunological reaction with said first and second antigens or antibodies, (d) separating the insolubilized sugar-bound lectin reaction product from the remainder of said reaction mixture, and (e) determining the amount of first and second label compounds in said insolubilized sugar-bound lectin product as a measure of the quantity of said first and second antigen in said sample.

41. A reaction product for use in an immunological assay comprising a labelled immunological reaction product in which one member of the reaction product is irreversibly bonded to a lectin and another member of the reaction product is irreversibly bonded to a label compound.

42. The reaction product of claim 41 in which said label compound is selected from the group consisting of enzyme, radioactive molecules, and fluorescent molecules.

43. The reaction product of claim 42 in which said label compound is an enzyme and the amount of said enzyme is determined by measuring its enzyme activity.

44. The reaction product of claim 41 reversibly bonded through said lectin to an insolubilized sugar on a solid surface, said sugar being selectively reactive with said lectin.

45. A reaction product for use in an immunochemical assay comprising a labelled immunological reaction product in which one member of the reaction product is irreversibly bonded to a sugar and another member of the reaction product is irreversibly bonded to a label compound.

46. The reaction product of claim 45 in which said label compound is selected from the group consisting of enzyme, radioactive molecules, and fluorescent molecules.

47. The reaction product of claim 46 in which said label compound is an enzyme and the amount of said enzyme is determined by measuring its enzyme activity.

48. The reaction product of claim 35 reversibly bonded through said sugar to an insolubilized lectin on a solid surface, said lectin being selectively reactive with said sugar.

* * * * *